US009675385B2

(12) United States Patent
Moskowitz et al.

(10) Patent No.: US 9,675,385 B2
(45) Date of Patent: Jun. 13, 2017

(54) SPINOUS PROCESS STAPLE WITH INTERDIGITATING-INTERLOCKING HEMI-SPACERS FOR ADJACENT SPINOUS PROCESS SEPARATION AND DISTRACTION

(75) Inventors: Mosheh T. Moskowitz, Rockville, MD (US); Ahmnon D. Moskowitz, Rockville, MD (US); Nathan C. Moskowitz, Rockville, MD (US)

(73) Assignee: Nathan C. Moskowitz, Rockville, MD (US)

( * ) Notice: Subject to any disclaimer, the term of this patent is extended or adjusted under 35 U.S.C. 154(b) by 0 days.

(21) Appl. No.: 13/101,135

(22) Filed: May 4, 2011

(65) Prior Publication Data

US 2011/0307011 A1 Dec. 15, 2011

Related U.S. Application Data

(63) Continuation-in-part of application No. 12/471,345, filed on May 22, 2009, now Pat. No. 8,257,370, and
(Continued)

(51) Int. Cl.
*A61B 17/70* (2006.01)
*A61B 17/064* (2006.01)
(Continued)

(52) U.S. Cl.
CPC ........ *A61B 17/7047* (2013.01); *A61B 17/068* (2013.01); *A61B 17/0642* (2013.01);
(Continued)

(58) Field of Classification Search
CPC ............ A61B 17/0642; A61B 17/0643; A61B 17/7047; A61B 17/7068; A61B 17/707; A61B 17/7062; A61F 2/4405
(Continued)

(56) References Cited

U.S. PATENT DOCUMENTS 4,554,914 A   11/1985 Kapp et al.
4,599,086 A    7/1986 Doty
(Continued)

FOREIGN PATENT DOCUMENTS

WO   2004093749 A1   11/2004
WO   2006091503 A1    8/2006

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Eduardo C Robert
*Assistant Examiner* — Julianna N Harvey
(74) *Attorney, Agent, or Firm* — Dresch IP Law, PLLC; John J. Dresch

(57) ABSTRACT

A Spinous Process (SP) staple including a top claw, a bottom claw, a staple pin pivotally connecting the top claw and the bottom claw, a ratchet mechanism that limits an opening force of the top claw with respect to the bottom claw, a first hemi-spacer positioned on the top claw and a second hemi-spacer positioned on the bottom claw. Upon the stapling of two adjacent spinous processes, the SP staple claws approximate, and the first and second hemi-spacers interdigitate, interlock, and unite to become a single interspinous process spacer which can be wedged between two adjacent spinous processes. Adjacent spinous process separation and/or distraction leading to spinal canal decompression and alleviation of the symptoms of spinal stenosis are accomplished.

57 Claims, 7 Drawing Sheets

Related U.S. Application Data a continuation-in-part of application No. 12/471,340, filed on May 22, 2009, now Pat. No. 8,734,516, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 12/471,345 is a continuation-in-part of application No. 12/054,335.

(60) Provisional application No. 60/670,231, filed on Apr. 12, 2005, provisional application No. 61/419,679, filed on Dec. 3, 2010, provisional application No. 61/425,749, filed on Dec. 21, 2010.

(51) Int. Cl.
*A61B 17/068* (2006.01)
*A61F 2/44* (2006.01)
*A61F 2/46* (2006.01)
*A61B 17/80* (2006.01)
*A61F 2/28* (2006.01)
*A61F 2/30* (2006.01)

(52) U.S. Cl.
CPC ...... *A61B 17/0643* (2013.01); *A61B 17/7065* (2013.01); *A61F 2/447* (2013.01); *A61F 2/4637* (2013.01); *A61B 17/809* (2013.01); *A61B 2017/0641* (2013.01); *A61B 2017/0647* (2013.01); *A61B 2017/0648* (2013.01); *A61F 2002/2835* (2013.01); *A61F 2002/305* (2013.01); *A61F 2002/30331* (2013.01); *A61F 2002/30383* (2013.01); *A61F 2002/30476* (2013.01); *A61F 2002/30772* (2013.01); *A61F 2002/30787* (2013.01); *A61F 2002/30879* (2013.01); *A61F 2002/448* (2013.01); *A61F 2002/4622* (2013.01); *A61F 2002/4641* (2013.01); *A61F 2220/0025* (2013.01); *A61F 2220/0033* (2013.01)

(58) Field of Classification Search
USPC ....... 606/249, 75, 324, 247, 248; 623/17.11, 623/17.16
See application file for complete search history.

(56) References Cited

U.S. PATENT DOCUMENTS

| | | |
|---|---|---|
| 4,636,217 A | 1/1987 | Ogilvie et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | MacMillan et al. |
| 5,123,926 A | 6/1992 | Pisharodi |
| 5,290,312 A | 3/1994 | Kojimoto et al. |
| 5,405,391 A | 4/1995 | Hednerson et al. |
| 5,413,583 A | 5/1995 | Wohlers |
| 5,454,819 A | 10/1995 | Knoepfler |
| 5,514,180 A | 5/1996 | Heggeness et al. |
| 5,660,188 A | 8/1997 | Groiso |
| 5,667,472 A | 9/1997 | Finn et al. |
| 5,782,832 A | 7/1998 | Larsen et al. |
| 5,865,848 A | 2/1999 | Baker |
| 5,888,223 A | 3/1999 | Bray, Jr. |
| 5,951,574 A | 9/1999 | Stefanchik et al. |
| 5,960,522 A | 10/1999 | Boe |
| 6,126,689 A | 10/2000 | Brett |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,572,653 B1 | 6/2003 | Simonson |
| 6,579,318 B2 | 6/2003 | Varga et al. |
| 6,582,468 B1 | 6/2003 | Gauchet |
| 6,613,055 B2 | 9/2003 | Di Emidio |
| 6,629,998 B1 | 10/2003 | Lin |
| 6,641,614 B1 | 11/2003 | Wagner et al. |
| 6,719,794 B2 | 4/2004 | Gerber |
| 6,723,126 B1 | 4/2004 | Berry |
| 6,733,532 B1 | 5/2004 | Gauchet et al. |
| 6,764,491 B2 | 7/2004 | Frey et al. |
| 6,770,094 B2 | 8/2004 | Fehling et al. |
| 6,824,564 B2 | 11/2004 | Crozet |
| 6,904,308 B2 | 6/2005 | Frisch et al. |
| 6,953,477 B2 | 10/2005 | Berry |
| 6,955,671 B2 | 10/2005 | Uchikubo |
| 6,972,019 B2 | 12/2005 | Michelson |
| 7,030,904 B2 | 4/2006 | Adair et al. |
| 7,033,394 B2 | 4/2006 | Michelson |
| 7,037,258 B2 | 5/2006 | Chatenever et al. |
| 7,097,615 B2 | 8/2006 | Banik et al. |
| 7,211,112 B2 | 5/2007 | Baynham et |
| 7,326,248 B2 | 2/2008 | Michelson |
| 7,442,209 B2 | 10/2008 | Michelson |
| 7,476,251 B2 * | 1/2009 | Zucherman et al. ...... 623/17.15 |
| 7,615,059 B2 | 11/2009 | Watschke et al. |
| 7,704,279 B2 * | 4/2010 | Moskowitz et al. ....... 623/17.11 |
| 7,862,616 B2 | 1/2011 | Lechmann et al. |
| 8,034,060 B2 | 10/2011 | Keren et al. |
| 8,206,420 B2 * | 6/2012 | Patel et al. ..................... 606/249 |
| 8,328,872 B2 | 12/2012 | Duffield et al. |
| 8,403,986 B2 | 3/2013 | Michelson |
| 2002/0068977 A1 | 6/2002 | Jackson |
| 2002/0143338 A1 | 10/2002 | Orbay et al. |
| 2004/0088054 A1 | 5/2004 | Berry |
| 2004/0177531 A1 | 9/2004 | DiBenedetto et al. |
| 2004/0254644 A1 | 12/2004 | Taylor |
| 2005/0027362 A1 | 2/2005 | Williams et al. |
| 2005/0049590 A1 | 3/2005 | Alleyne et al. |
| 2005/0177235 A1 | 8/2005 | Baynham et al. |
| 2005/0216084 A1 | 9/2005 | Fleischmann et al. |
| 2005/0240188 A1 * | 10/2005 | Chow et al. ..................... 606/72 |
| 2005/0273170 A1 | 12/2005 | Navarro et al. |
| 2005/0278026 A1 | 12/2005 | Gordon et al. |
| 2007/0161992 A1 * | 7/2007 | Kwak et al. ..................... 606/61 |
| 2007/0213820 A1 | 9/2007 | Magerl et al. |
| 2007/0270840 A1 * | 11/2007 | Chin et al. ........................ 606/61 |
| 2008/0294206 A1 * | 11/2008 | Choi et al. .................. 606/86 A |
| 2009/0054988 A1 * | 2/2009 | Hess .......................... 623/17.16 |
| 2009/0105831 A1 | 4/2009 | Jones et al. |
| 2009/0163920 A1 * | 6/2009 | Hochschuler et al. .......... 606/74 |
| 2010/0087860 A1 * | 4/2010 | Chin et al. ..................... 606/249 |
| 2010/0145460 A1 | 6/2010 | McDonough et al. |
| 2011/0022090 A1 * | 1/2011 | Gordon et al. ............... 606/249 |
| 2011/0066186 A1 * | 3/2011 | Boyer et al. ................. 606/249 |
| 2011/0144692 A1 * | 6/2011 | Saladin et al. ................ 606/249 |
| 2011/0313458 A1 * | 12/2011 | Butler et al. .................. 606/249 |
| 2012/0029636 A1 * | 2/2012 | Ragab et al. ............... 623/17.11 |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. To Aug. 1, 2003, pp. S15-S23.

Dieter Grob et al., "Clinical Experience With the Dynesys Semirigid Fixation System for the Lumbar Spine," SPINE, vol. 30, No. 3, 2005, pp. 324-331.

(56) References Cited

OTHER PUBLICATIONS

International Search Report (ISR) and Written Opinion of the International Searching Authority, Dec. 3, 2007, International Application No. PCT/US 07/05005.

International Search Report (ISR) and Written Opinion of the International Searching Authority, May 21, 2008, International Application No. PCT/US2007/021015.

International Search Report (ISR) and Written Opinion of the International Searching Authority, Jul. 9, 2008, International Application No. PCT/US2007/021013.

* cited by examiner

SPINOUS PROCESS STAPLE WITH INTERDIGITATING-INTERLOCKING HEMI-SPACERS FOR ADJACENT SPINOUS PROCESS SEPARATION AND DISTRACTION

CROSS-REFERENCE TO RELATED APPLICATIONS

This application is a Continuation-In-Part Application of co-pending application Ser. No. 12/471,345, filed on May 22, 2009 and co-pending application Ser. No. 12/471,340, filed on May 22, 2009, each of which is a Continuation-In-Part Application of co-pending application Ser. No. 12/054,335, filed on Mar. 24, 2008, which is a Continuation-In-Part of application Ser. No. 11/842,855, filed on Aug. 21, 2007, which is a Continuation-In-Part of application Ser. No. 11/536,815, filed on Sep. 29, 2006 (now U.S. Pat. No. 7,846,188), which is a Continuation-In-Part of application Ser. No. 11/208,644, filed on Aug. 23, 2005 (now U.S. Pat. No. 7,704,279), and this application also claims priority under 35 U.S.C. 119(e) of U.S. Provisional Application No. 60/670,231, filed on Apr. 12, 2005, U.S. Provisional Application No. 61/419,679, filed on Dec. 3, 2010, and U.S. Provisional Application No. 61/425,749, filed on Dec. 21, 2010; the entire contents of all the above identified patent applications are hereby incorporated by reference in their entirety.

This application is related to applicant's co-pending U.S. application, filed concurrently herewith, titled "INTERARTICULATING SPINOUS AND TRANSVERSE PROCESS STAPLES FOR SPNAL FUNSION", Ser. No. 13/101,129, which is incorporated herein by reference in its entirety.

FIELD OF DISCLOSURE

The present invention relates to a Spinous Process (SP) staple with interdigitating-interlocking hemi-spacers which simultaneously staple and separate/distract two adjacent Spinous Processes (SPs), thereby decompressing the spinal canal and effectively treating the clinical symptoms of lumbar stenosis in a minimally invasive manner.

BACKGROUND

Lumbar stenosis is a painful condition which compresses nerves and leads to back and leg pain. Traditionally this condition has been and is treated by a lumbar laminectomy with or without spinal fusion. A laminectomy entails the open surgical removal of lamina which decompresses the spinal canal and its nerves thereby alleviating symptoms. This procedure is done under general anesthesia, can be complicated by infection, spinal fluid leak, nerve injury, blood loss, infection etc. When a laminectomy is performed in conjunction with an instrumented pedicle screw fusion, the risks and complications are further increased, and are yet even further magnified in elderly individuals who commonly suffer from this condition.

Recent attention has been focused on minimally invasive techniques to alleviate lumbar stenosis. In particular, recent inventions include a variety of interspinous spacers which can be wedged in between spinous processes, and secured via adjustable wings to the adjacent SPs. This procedure keeps the adjacent SPs distracted even in the standing position, mimicking the flexed position, and hence in some cases relieves the symptoms of spinal stenosis. The most notable invention of this kind is the X-Stop (Zucherman et. al. Interspinous Process Apparatus and Method with a selectably expandable spacer; U.S. Pub. No. 2007/0093830 A1 Apr. 26, 2007) which consists of two adjustable wings attached to an adjustable interspinous spacer.

Applicants' related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, each of which are hereby incorporated by reference, relate to interarticulating staples accomplishing Facet Joint (FJ), Spinous Process (SP), and Transverse Process (TP) fusion employing minimally invasive techniques. The embodiments described herein are modifications of a Spinous Process (SP) staple device, and incorporate interdigitating-interlocking hemi-spacers onto the top and bottom claws of the SP staple in between two sets of staple prongs which insert into two adjacent SPs. When the staple claws are clamped onto the two adjacent SPs, the intervening interlocked top and bottom claw hemi-spacers can unite to form a single spacer, and can be wedged in between the adjacent SPs, separating and distracting them, thereby relieving lumbar stenosis.

Placement of the exemplary devices can be done with local anesthesia, and through a small incision. As opposed to the X-stop, and similar devices, an exemplary device according to the invention is a one piece device (upon application) that merely has to be fastened onto adjacent SPs and clamped with a staple applier using a solitary one-step-procedure. This invention continues to further advance minimally invasive and low risk spinal device technology.

SUMMARY

Herein described is an exemplary embodiment of a Spinous Process (SP) staple and separating/distracting device. The exemplary embodiments take into account the inter-SP distance, and the geometric contour, topography, and bone thickness of the SP elements. The present invention recognizes the aforementioned problems with conventional apparatus and solves these problems by, among other things, improving upon the designs illustrated in the aforementioned related applications. The exemplary embodiments provide an advanced minimally invasive and low risk method of adjacent SP separation/distraction.

The exemplary embodiment of the Spinous Process (SP) staple with interlocking-interdigitating hemi-spacers whether performed via open, endoscopic, or percutaneous fluoroscopically guided surgical techniques when compared to a laminectomy with or without fusion entails far less muscle retraction, blood loss and significant reduction in operating room time. Thus, the complications of nerve and or vascular injury, facet joint violation, worsening spinal instability, and pedicle screw pull out, are all obviated. When compared to the X-Stop and similar devices, surgical application of this single-piece device (upon application) utilizes a solitary one-step procedure thereby enhancing its minimal invasive utility, and further economizes operating room time. It can be done under local anesthesia in an out-patient setting.

The exemplary embodiment of this device can be used to perform multiple levels of distraction engaging a series of adjacent pair of SPs with one staple per unit of two adjacent elements. These embodiments can be employed to adjoin, separate and distract multiple levels of SPs in incremental spinal process units of two.

For example, an exemplary embodiment of the SP staple with interlocking-interdigitating hemi-spacers may include a top claw and a bottom claw with a plurality of ridges, a staple pin pivotally connecting the top claw and the bottom claw, and a ratchet mechanism that limits an opening force of the top claw with respect to the bottom claw. The ratchet mechanism includes a ratchet pin pivotably mounted to the top claw, wherein the claws include a plurality of claw teeth which interdigitate with each other, and wherein the ratchet pin includes a flexure spring engaging the plurality of ratchet teeth. The plurality of claw ridges helps incorporate it into the bone.

The staple's top and bottom claws may also include a plurality of prongs. Further, there may be two sets of upper and lower claw prongs designed for penetration of each SP. The distance between these two sets of prongs is the average distance between lumbar SPs. The staple can be manufactured with varying interspinous distances to address varying intra and inter-patient anatomical differences.

In an embodiment, a total of sixteen prongs may be utilized; eight prongs per SP unit. Further, a total of eight prongs on the upper claw and eight prongs on the lower jaw may be utilized; four prongs on the upper claw for penetration of each SP and four prongs on the lower claw for penetration of each SP. The staple on two adjacent SPs may be clamped using a total of eight prongs to penetrate each SP; four from the upper claw, and four from the bottom claw. The two sets of prongs per SP unit can be spaced apart on the upper and lower claws at a distance equal to the interspinous process distance such that the claws will engage and perforate each adjacent SP. Other embodiments may utilize multiple variations of the number and precise location of the prongs.

In between the two sets of prongs on the upper and lower claws is a rectangular hemi-spacer that can be attached to each claw with a screw and can be positioned to act as a wedge occupying the inter-spinous space in between adjacent SPs. The hemi-spacers on opposing staple claws are designed with mirror image interlocking protrusions, and protrusion receptacles allowing their co-mating and thus unification. Thus, when the upper and lower claws of the SP staple unite, and their prongs perforate adjacent SPs, the hemi-spacers interdigitate, interlock, and unite forming a single interspinous process wedge spacer which maintains separation/distraction between SPs, thereby alleviating spinal canal compression thus alleviating lumbar stenosis.

The hemi-spacers can be attached to each claw of the staple via a screw. Depending on the interspinous distance, and the degree of desired SP separation/distraction, different sized hemi-spacers can be preferentially attached to each claw to account for inter- and intra-patient anatomical variability. The size can vary in height, length and width. The staples can be manufactured with built-in non-removable hemi-spacers. The hemi-spacers may be any suitable geometric shape to achieve SP separation e.g., square, elliptical, ovoid, triangular, pentagonal, hexagonal, or others. The hemi-spacer interdigitations can also be composed of sharp penetrating prongs, of a series of horizontal or vertical extensions which can fit into corresponding slots, or any similar mating technique which can align and unite two mirror image masses. The hemi-spacers and the staple can be made of any bio-compatible material.

Furthermore the staples can be manufactured with different claw lengths and inter-spinous inter-prong distances.

In related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, Applicants have described various exemplary embodiments of staple prongs, including solid-straight, solid-curved, perforated-straight and perforated-curved staple prongs.

Perforated prongs may include multiple perforations within the prongs themselves which can allow the packing of autologous, or allograft bone, bone putty, bone morphogenic protein, bmp, bone marrow aspirate or any biological or synthetic material which promotes bone fusion. Further, these embodiments can facilitate integration of the device into the bone and promote bony fusion. The curved or straight prong(s) embodiments can be selected based on anatomical variations and surgical preference. These embodiments can be applied to this staple as well. Only the solid-straight embodiment is illustrated here. The other prong embodiments are incorporated here by reference.

The exemplary embodiment of this device can be used to perform multiple levels of separation/distraction engaging a series of adjacent pair of SPs with one staple per every incremental unit of two adjacent SP elements.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE EXEMPLARY EMBODIMENTS

Aspects of the invention are disclosed in the following description and related drawings directed to specific embodiments of the invention. Alternate embodiments may be devised without departing from the scope of the invention. Additionally, well known elements of the invention will not be described in detail or will be omitted so as not to obscure the relevant details of the invention.

The word "exemplary" is used herein to mean "serving as an example, instance, or illustration". Any embodiment described herein as "exemplary" is not necessarily to be construed as preferred or advantageous over other embodiments. Likewise the term "embodiments of the invention" does not require that all embodiments of the invention include the discussed feature, advantage or mode of operation.

With reference to FIGS. 1-3 exemplary embodiments of the invention will now be described.

1. Exemplary Medical Device

Referring to FIGS. 1-3, the above described problems of the conventional art can be solved in the thoracic, lumbar and cervical spine.

Figure 1A:
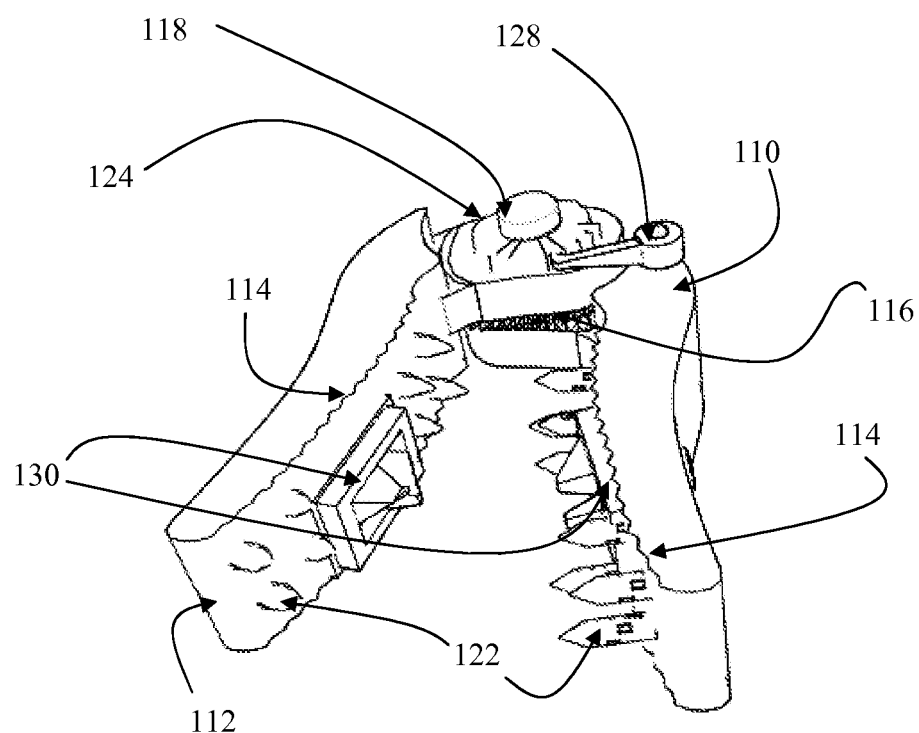
FIG. 1A illustrates a perspective (top oblique) view of the SP staple in an open position, according to an exemplary embodiment of the invention.
Figure 1B:
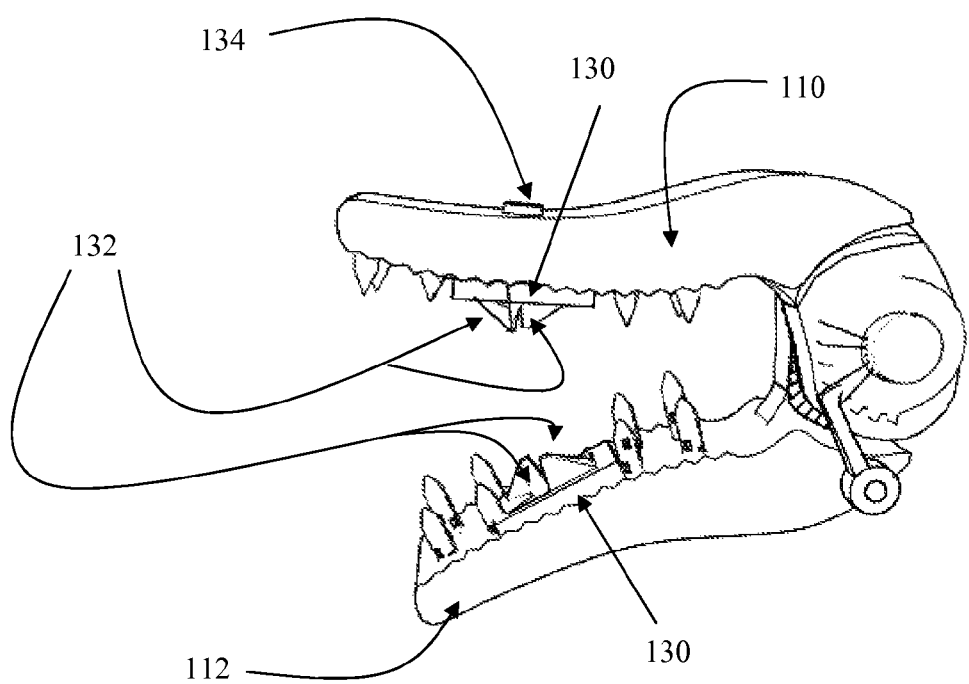
FIG. 1B illustrates a perspective (lateral) view of the SP staple in an open position, according to an exemplary embodiment of the invention.

For example, FIGS. 1A-B illustrate three dimensional views of an embodiment of the Spinous Process (SP) staple apparatus 100a.

FIGS. 1A-B illustrate an embodiment of a Spinous Process (SP) staple with interdigitating-interlocking hemi-spacers, for example, including a flexure spring (e.g., ratchet pawl 128). As shown in FIGS. 1A-B, the features of the staple 100 can include top claws 110 and bottom claws 112 with claw ridges 114 to help incorporate and fuse with bone. A staple pin-pivot 118 can connect the top claws 110 and bottom claws 112. The staple 100 may include fastener pins/prongs 122 to help incorporate and fuse with bone; however, the staple 100 is not limited to any number of fastener pins/prongs 122. For example, in the illustrated embodiments, the staple 100 includes sixteen fastener pins/prongs 122; eight per the top claw 110 and eight per the bottom claw 112. Further, a total of eight prongs for engagement of two segmental SPs may be utilized such that each SP may be penetrated and perforated by a total of eight prongs; four prongs per single SP unit of penetration/engagement on the top claw 110 and four prongs per single SP unit of penetration/engagement on the bottom claw. However, in other embodiments, the staple 100 can include other amounts of fastener pins/prongs 122, such as four, six, eight, ten, etc. for engagement of the segmental SPs.

Claw teeth 116 may be molded onto the top claw 110 and bottom claw 112, and the claw teeth 116 may be interdigitating. Further, ratchet teeth 124 may be molded onto the bottom claw 112 (shown in FIG. 1A), and a ratchet pawl 128 (e.g., spring loaded ratchet pawl) may interact with the ratchet teeth 124 locking the staple 100 in position. The ratchet pawl 128 can be connected to the top claw 110 via ratchet bolt 120 and can rotate about the ratchet bolt 120 (shown in FIG. 1A).

In another embodiment, ratchet teeth 124 may also be molded on the top claw 110 (shown in FIG. 1B), and the ratchet pawl 128 may interact with the ratchet teeth 124 locking the staple 100 in position. The ratchet pawl 128 can be connected to the bottom claw 112 via ratchet bolt 120 and can rotate about the ratchet bolt 120 (shown in FIG. 1B).

As the staple 100 closes, the ratchet pawl 128 works in standard fashion. When a force is applied to open the staple 100, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100 by a force proportional to the stiffness of the ratchet pawl 128 (e.g., flexure spring). Further, the force can be tailored by making the ratchet pawl 128 from different materials or varying the dimension(s) of the ratchet pawl 128. This embodiment can achieve significant rigidity (stiffness).

The interior surfaces and/or exterior surfaces of the top claw 110 and bottom claw 112 can include hemi-spacer(s) 130. As shown in FIGS. 1A-B, the hemi-spacer(s) 130 can be positioned on the interior surfaces of the top claw 110 and bottom claw 112 such that when the staple 100 is closed, the hemi-spacer(s) 130 are positioned on opposing surfaces of each other. Each hemi-spacer 130 can be attached to the top claw 110 and bottom claw 112, for example, with a screw 134 or other suitable fixing device. Further, the shape of the hemi-spacer(s) 130 can vary. For example, in the illustrated embodiments, the staple 100 includes hemi-spacer(s) 130 that are rectangular in shape. However, in other embodiments, the hemi-spacers 130 can include other shapes, such as circular, oval, square, etc. In other embodiments, a thickness of the hemi-spacer 130 on one claw can be greater than a thickness of the hemi-spacer 130 on the other claw. In still other embodiments, the hemi-spacer 130 can be formed on only one of the claws 110, 112.

Further, each hemi-spacer 130 can include interdigitating prongs 132 which can be used to interdigitate, interlock, and unite with corresponding features on another hemi-spacer 130, thereby forming a single interspinous process spacer wedge. The wedge (hemi-spacer pair 130) can occupy and maintain the inter-spinous space in between adjacent Spinous Processes (SPs), thereby alleviating spinal canal compression and any ensuing lumbar stenosis.

Figure 3A:
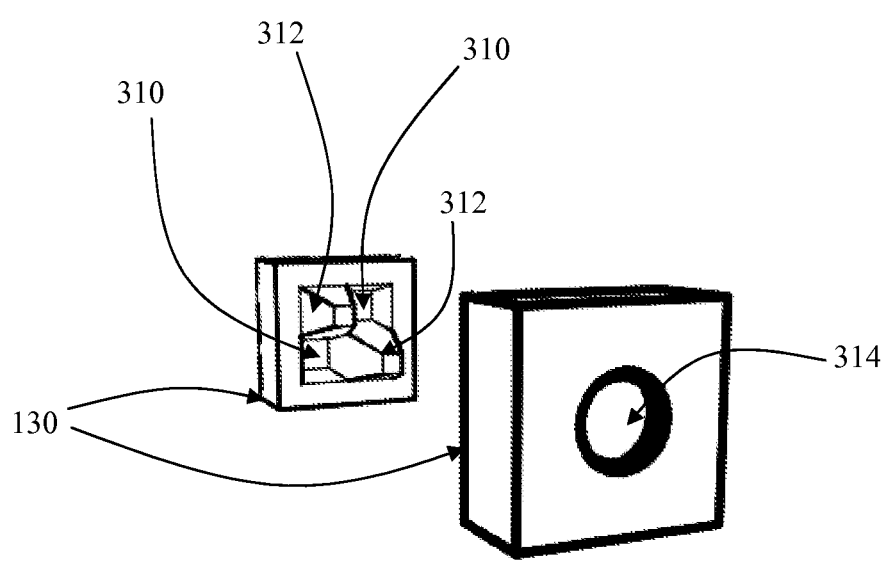
FIG. 3A illustrates a perspective view of two opposing hemi-spacers, according to an exemplary embodiment of the invention.
Figure 3B:
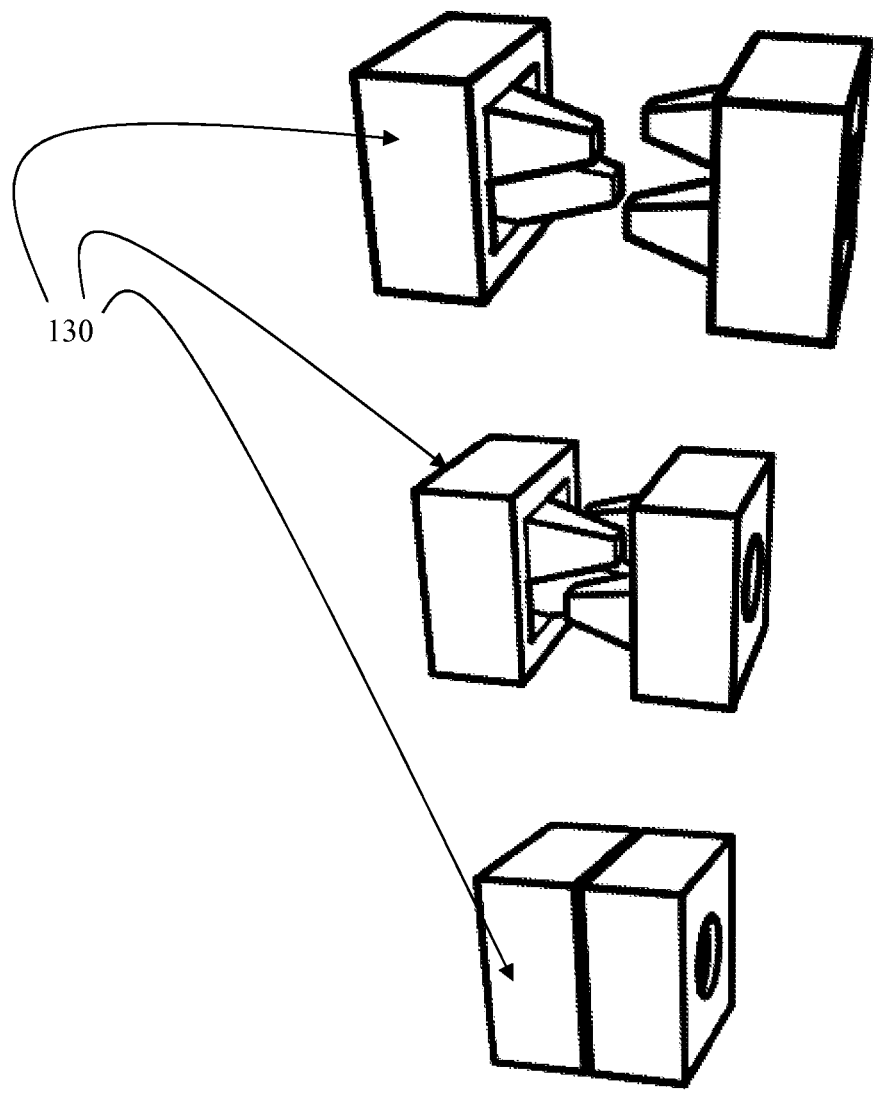
FIG. 3B illustrates a perspective view of sequential interdigitation of opposing hemi-spacers forming a united single interspinous spacer wedge, according to an exemplary embodiment of the invention.

In another exemplary embodiment, each hemi-spacer 130 positioned on opposing staple claws (110, 112) can include interdigitating prongs 132. The interdigitating prongs 132 may include mirror image interlocking protrusions 312 (FIGS. 3A-B) and protrusion receptacles 310 (FIGS. 3A-B). The interlocking protrusions 312 and protrusion receptacles 310 can interact allowing for co-mating and unification of each hemi-spacer 130. Thus, when the top claw 110 and bottom claw 112 of the SP staple 100 are closed (i.e. unit), the fastener prongs 122 will perforate adjacent SPs and the hemi-spacer(s) 130 (and interlocking protrusions 312 and protrusion receptacles 310) will interdigitate, interlock, and unite forming a single interspinous process spacer wedge which maintains separation distraction between SPs, thereby alleviating spinal canal compression thus alleviating lumbar stenosis.

The hemi-spacers 130 can be attached to each claw 110, 112 of the staple 100, for example, via a screw 134 or other suitable fixing device. Further, different sized hemi-spacers 130 can be selectively and preferentially attached to each claw 110, 112 to account for inter- and intra-patient anatomical variability depending on the interspinous distance. The staples 100 also can be manufactured with various tolerances, e.g. different claw lengths and inter-spinous inter-prong distances, etc. The exemplary embodiments disclosed herein can be used to perform multiple levels of distraction engaging a series of adjacent pair of SPs with one staple 100 per every incremental unit of two adjacent SP elements.

Figure 2A:
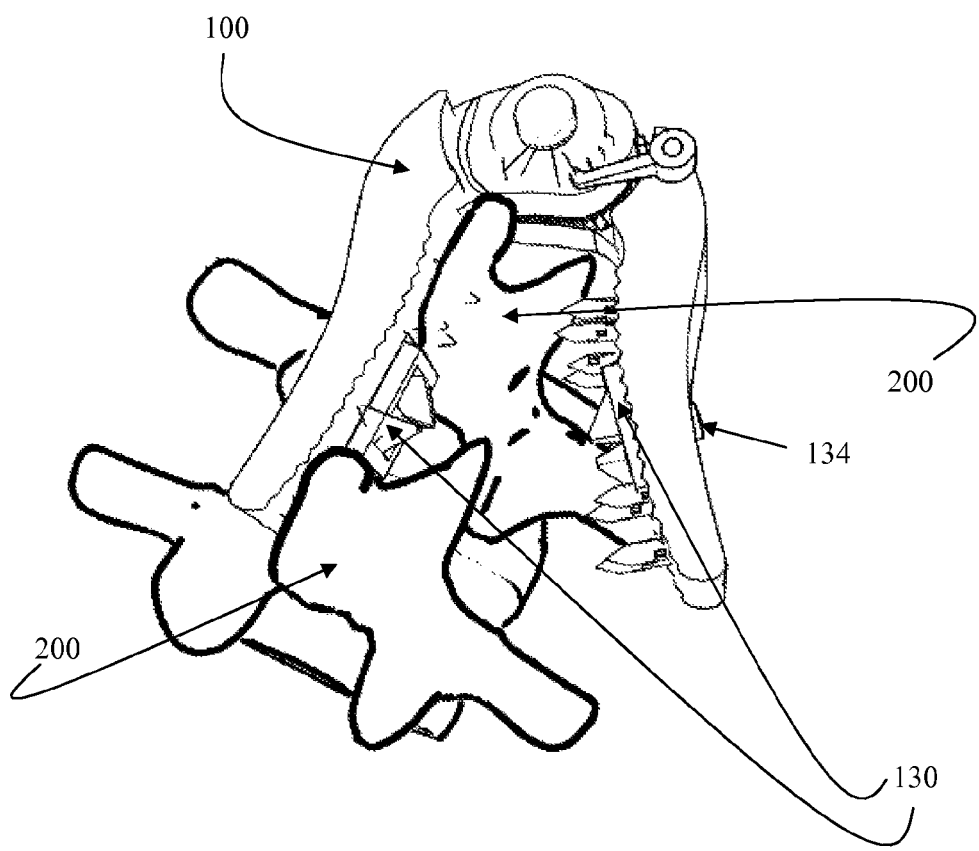
FIG. 2A illustrates a perspective assembly (top oblique) view of the SP staple articulating with two SPs in an open position (wide open), according to an exemplary embodiment of the invention.
Figure 2B:
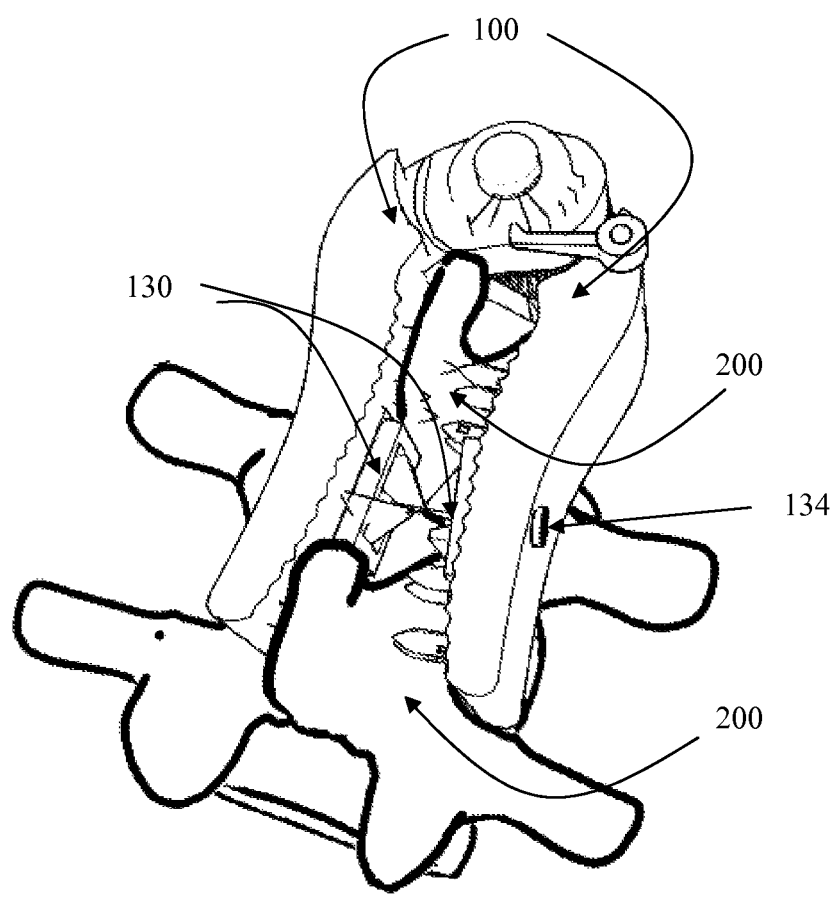
FIG. 2B illustrates a perspective assembly (top oblique) view of the SP staple articulating with two SPs in a partially open position (partially clamped), according to an exemplary embodiment of the invention.
Figure 2C:
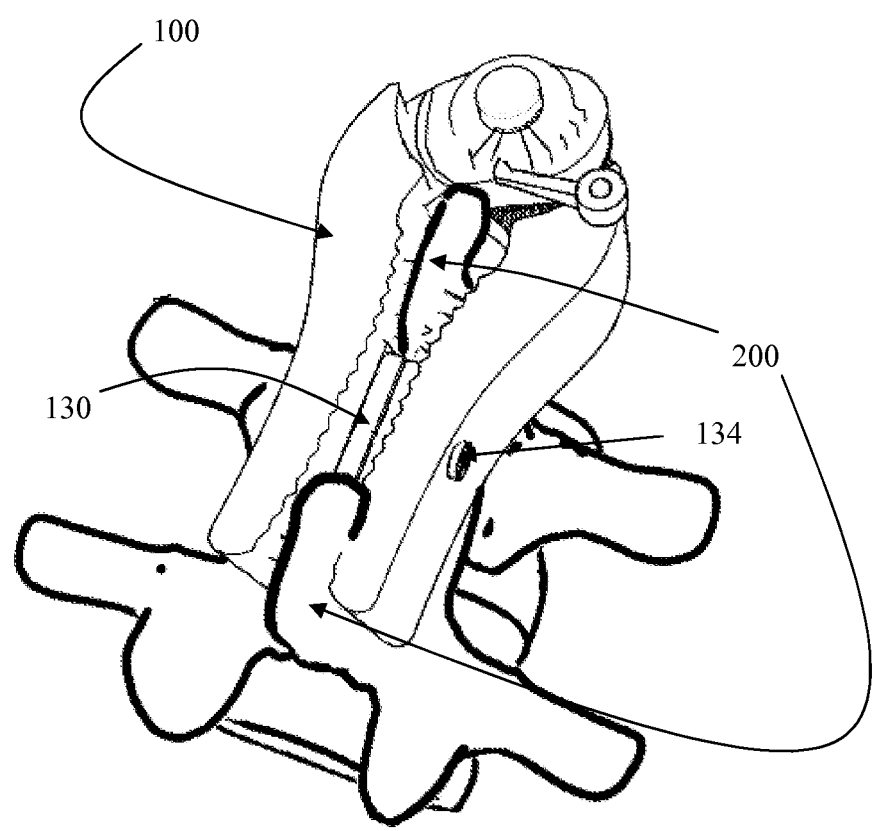
FIG. 2C illustrates a perspective assembly (top oblique) view of the SP staple articulating with two SPs in a closed position, according to an exemplary embodiment of the invention.

FIGS. 2A-C illustrate an exemplary embodiment of a step-by-step mechanical engagement of the SP staple 100 with two segmental SPs 200; beginning with the staple's opened position (FIG. 2A), then subsequently progressing to a semi-closed position (FIG. 2B), and then subsequently and finally achieving a fully clamped position (FIG. 2C) entirely engaging and unifying the two segmental SPs 200. The hemi-spacer(s) 130 may include mirror image interlocking protrusions 312 (FIGS. 3A-B) and protrusion receptacles 310 (FIGS. 3A-B). The interlocking protrusions 312 and protrusion receptacles 310 can interact allowing for co-mating and unification of each hemi-spacer 130. Thus, when the top claw 110 and bottom claw 112 of the SP staple 100 are closed (i.e., clamped), the fastener prongs 122 will perforate adjacent SPs 200 and the hemi-spacer(s) 130 (and interlocking protrusions 312 and protrusion receptacles 310) will interdigitate, interlock, and unite forming a single interspinous process spacer wedge which maintains separation distraction between SPs 200, thereby alleviating spinal canal compression thus alleviating lumbar stenosis.

FIG. 3A illustrates an exemplary embodiment of the hemi-spacer(s) 130 located on opposing staple claws 110, 112. Each hemi-spacer(s) 130 can include one or more hemi-spacer screw inserts 314. Each hemi-spacer(s) 130 can be attached to the top claw 110 and bottom claw 112, for example via one or more screws 134, which can be secured in the one or more hemi-spacer screw inserts 314 and can penetrate one or more perforations (not illustrated) on each claw 110, 112. In the illustrated exemplary embodiment, each hemi-spacer 130 includes a single hemi-spacer screw insert 314, and each hemi-spacer 130 is attached to the top claw 110 and bottom claw 112, respectively, using a single screw 134, which is secured in the hemi-spacer screw insert 314 and penetrates a single perforation (e.g., screw hole or threaded screw hole) (not illustrated) on each claw 110, 112. In other embodiments, the hemi-spacers 130 can be integrally formed with the claws 110, 112. In other embodiments, the hemi-spacers 130 can be permanently or removably/replaceably fixed to the claws 110, 112 by other suitable fixing means.

As shown in FIG. 3A, in an exemplary embodiment, a surface of each hemi-spacer 130 can include two mirror image interdigitating protrusions 312 and two mirror image protrusion receptacles 310 which mate with corresponding features on an opposing hemi-spacer 130 when the hemi-spacers 130 are aligned. However, in other embodiments, the hemi-spacer(s) 130 can include any number of mirror image interdigitating protrusions 312 and corresponding mirror image protrusion receptacles 310 which mate with each other when aligned.

FIG. 3B illustrates an exemplary embodiment of the hemi-spacer(s) 130 whereby two opposing hemi-spacer(s) 130 can unify into a single inter-spinous wedge spacer. For example, in the illustrated embodiments, the mirror image interdigitating protrusions 312 of each opposing hemi-spacer 130 interdigitates and mates with an opposing mirror image protrusion receptacle 310 of the corresponding hemi-spacer 130. The interdigitating protrusions 312 and their corresponding protrusion receptacles 310 of each hemi-spacer 130 can mate with each other forming a unified interspinous spacer-wedge.

The exemplary staples 100 can be provided with a variety of inter-prong distances to account for inter and intra-patient inter-spinous distance variations. The hemi-spacers 130 can be formed with different dimensions, such as a variety of heights, lengths, and widths, to account for variations in dimensions between patients.

The protrusions 312 and protrusion receptacles 310 of the hemi-spacer 130 can have a variety of corresponding shapes. For example, as illustrated in the exemplary embodiments, the sidewalls of the protrusions 312 and protrusion receptacles 310 can have a tapered shape to facilitate easy alignment and engagement/mating therebetween. In other embodiments, the sidewalls of the protrusions 312 and protrusion receptacles 310 can have other shapes, such as conical shapes, pyramid shapes, triangular shapes, square shapes, rectangular shapes, etc.

2. Exemplary Surgical Method

Exemplary surgical steps for practicing one or more of the foregoing embodiments will now be described.

Surgical implantation of the Spinous Process (SP) staple with interdigitating-interlocking hemi-spacers conjoining and separating/distracting two adjacent SPs can be performed under standard open, closed, percutaneous, endoscopic, tubular, microscopic, fluoroscopic or any other standardized techniques. The SP staple can be applied to and engaged with a staple gun whose design has been described in, for example, Applicants' related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, relating to the FJ staple, herein incorporated by reference. The staple gun can have a straight distal applier or angled applier to facilitate placement depending on the particular spinal anatomy. The patient may be positioned prone and flexed or lateral and flexed. After the administration of local anesthesia with or without Intravenous (IV) sedation or any acceptable form of analgesia/anesthesia, an incision is made over the desired adjacent SPs. The interspinous ligament may be partially or completely opened or separated. Upon exposure of two adjacent SP processes, the staple 100 is opened via the staple gun applier, the two adjacent SPs are engaged by the opened staple claws 110, 112, and the staple gun then closes the upper and lower claws 110, 112 which lead to the stapling of the two adjacent SPs (FIGS. 2A-C). The closure of the staple 100 leads to the unification of the two hemi-spacers 130 into one spacer wedge which separates and distracts the adjacent SPs (FIGS. 2A-C and FIGS. 3A-B). A variety of staples 100 can be manufactured with varying inter-prong distances to account for inter and intra-patient inter-spinous distance variations. The staple 100 with the correct approximate inter-spinous prong distance is selected. The hemi-spacers 130 with the desired height, length, and width are selected and may be attached to the staple claws 110, 112 prior to SP stapling. Staples 100 can also be manufactured with different sized hemi-spacers 130 already secured to the claws 110, 112, thereby not necessitating that the surgeon need to fiddle with placement of the hemi-spacers 130 on the staple 100, for example, by attaching with screws 134 (i.e., the hemi-spacers 130 can be pre-installed on the claws 110, 112 of the staple 100). Alternatively, in other embodiments staples 100 with built-in (not screwed in) hemi-spacers 130 of differing dimensions can be selected for different patients.

In between the two sets of prongs 122 on the upper and lower claws 110, 112 is an attached rectangular hemi-spacer 130. It is positioned to act as a wedge occupying the inter-spinous space in between adjacent SPs. The hemi-spacers 130 on opposing staple claws 110, 112 are designed with mirror image interlocking protrusions 312, and protrusion receptacles 310 allowing their co-mating and thus unification (FIGS. 3A-B). Thus when the upper and lower claws 110, 112 of the SP staple 100 unite, and their prongs 122 perforate adjacent SPs, the hemi-spacers 130 interdigitate, interlock, and unite forming a single interspinous process spacer wedge which maintains distraction between SPs, thereby alleviating spinal canal compression thus alleviating lumbar stenosis (FIGS. 2A-C).

The hemi-spacers are attached to each claw of the staple via a screw. Depending on the interspinous distance, different sized hemi-spacers (differing in length, height and/or width) can be preferentially attached to each claw to account for inter- and intra-patient anatomical variability.

Furthermore the staples themselves can be manufactured with different claw lengths and inter-spinous inter-prong distances. Hemi-spacers can be designed in any variety of geometric shape, and mate with any form of interlocking mechanisms entailing extrusions slots, prongs, pins etc.

The exemplary embodiment of this device can be used to perform multiple levels of distraction engaging a series of adjacent pair of SPs with one staple per every incremental unit of two adjacent SP elements.

A surgeon can select the degree of adjacent SP separation and distraction by choosing hemi-spacers of increasing lengths.

In another embodiment, an interarticulating staple 100 can be provided for clamping one of a thoracic/lumbar Spinous Process (SP), a thoracic/lumbar Transverse Process (TP), and cervical Spinous Process (SP). The interarticulating staple 100 can include a top claw 110, a bottom claw 112, a staple pin 118 pivotally connecting the top claw 110 and the bottom claw 112, and ratchet means (e.g., 124, 128) for limiting an opening force of the top claw 110 with respect to the bottom claw 112. The staple 100 can include spacer means (e.g., 130) on the top claw 110 and/or on the bottom claw 112 for providing adjacent spinous process separation and/or distraction. Upon the stapling of two adjacent spinous processes, the staple claws approximate, and the spacer means can be wedged between two adjacent spinous processes, thereby providing adjacent spinous process separation and/or distraction leading to spinal canal decompression and alleviation of the symptoms of spinal stenosis.

In another embodiment, an interarticulating staple 100 can be provided for clamping one of a thoracic/lumbar Spinous Process (SP), a thoracic/lumbar Transverse Process (TP), and cervical Spinous Process (SP). The interarticulating staple 100 can include first claw means (e.g., 110) pivotally connected to second claw means (e.g., 112); and ratchet means (e.g., 124, 128) for limiting an opening force of the first claw means (e.g., 110) with respect to the second claw means (e.g., 112) and fixing a position of the first claw means (e.g., 110) with respect the second claw means (e.g., 112); and spacer means (e.g., 130) on at least one of the first claw means (e.g., 110) and the second claw means (e.g., 112), the spacer means for providing one of adjacent spinous process separation and distraction. Upon the stapling of two adjacent spinous processes, the staple claws approximate, and the spacer means can be wedged between two adjacent spinous processes, thereby providing adjacent spinous process separation and/or distraction leading to spinal canal decompression and alleviation of the symptoms of spinal stenosis.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

What is claimed is:

1. An interarticulating staple for clamping one of a thoracic/lumbar Spinous Process (SP), a thoracic/lumbar Transverse Process (TP), and cervical Spinous Process (SP), the interarticulating staple comprising:
    a first claw having a first clamping surface;
    a second claw having a second clamping surface;
    a staple pin pivotally connecting the first claw and the second claw;
    a ratchet mechanism that limits an opening force of the first claw with respect to the second claw;
    a first hemi-spacer on the first clamping surface of the first claw; and
    a second hemi-spacer on the second clamping surface of the second claw and opposed to the first hemi-spacer when the first claw and the second claw are in a closed position.

2. The staple according to claim 1, wherein the ratchet mechanism comprises:
    a ratchet pin pivotably mounted to the first claw,
    wherein the second claw includes a plurality of ratchet teeth, and
    wherein the ratchet pin includes a flexure spring engaging the plurality of ratchet teeth.

3. The staple according to claim 1, wherein the ratchet mechanism comprises:
    a ratchet pin pivotably mounted to the second claw,
    wherein the first claw includes a plurality of ratchet teeth, and
    wherein the ratchet pin includes a flexure spring engaging the plurality of ratchet teeth.

4. The staple according to claim 1, wherein the first clamping surface includes a plurality of ridges.

5. The staple according to claim 4, wherein the plurality of ridges are formed on the first clamping surface on opposite sides of the first hemi-spacer.

6. The staple according to claim 1, wherein the second clamping surface includes a plurality of ridges.

7. The staple according to claim 6, wherein the plurality of ridges are formed on the second clamping surface on opposite sides of the second hemi-spacer.

8. The staple according to claim 1, wherein the first clamping surface includes a plurality of prongs.

9. The staple according to claim 8, wherein the plurality of prongs are formed on the first clamping surface on opposite sides of the first hemi-spacer.

10. The staple according to claim 8, wherein the first hemi-spacer is positioned in between the plurality of prongs.

11. The staple according to claim 10, wherein the plurality of prongs on the first claw are separated into a first group of prongs and a second group of prongs, and
    wherein the first group of prongs is separated from the second group of prongs by a distance approximately equal to an inter-spinous process distance.

12. The staple according to claim 10, wherein the plurality of prongs on the first claw are separated into a first group of prongs and a second group of prongs, and
    wherein the first group of prongs is separated from the second group of prongs by a distance approximately equal to an inter-lumbar transverse process distance.

13. The staple according to claim 8, wherein the plurality of prongs on the first claw are separated into a first group of prongs and a second group of prongs, and
    wherein the first group of prongs is separated from the second group of prongs by a distance approximately equal to an inter-spinous process distance.

14. The staple according to claim 8, wherein the plurality of prongs on the first claw are separated into a first group of prongs and a second group of prongs, and
    wherein the first group of prongs is separated from the second group of prongs by a distance approximately equal to an inter-lumbar transverse process distance.

15. The staple according to claim 1, wherein the second clamping surface includes a plurality of prongs.

16. The staple according to claim 15, wherein the plurality of prongs are formed on the second clamping surface on opposite sides of the second hemi-spacer.

17. The staple according to claim 15, wherein the second hemi-spacer is positioned in between the plurality of prongs.

18. The staple according to claim 17, wherein the plurality of prongs on the second claw are separated into a first group of prongs and a second group of prongs, and
wherein the first group of prongs is separated from the second group of prongs by a distance approximately equal to an inter-spinous process distance.

19. The staple according to claim 17, wherein the plurality of prongs on the second claw are separated into a first group of prongs and a second group of prongs, and
wherein the first group of prongs is separated from the second group of prongs by a distance approximately equal to an inter-lumbar transverse process distance.

20. The staple according to claim 15, wherein the plurality of prongs on the second claw are separated into a first group of prongs and a second group of prongs, and
wherein the first group of prongs is separated from the second group of prongs by a distance approximately equal to an inter-spinous process distance.

21. The staple according to claim 15, wherein the plurality of prongs on the second claw are separated into a first group of prongs and a second group of prongs, and
wherein the first group of prongs is separated from the second group of prongs by a distance approximately equal to an inter-lumbar transverse process distance.

22. The staple according to claim 1, wherein the first hemi-spacer is secured to the first claw with a screw.

23. The staple according to claim 22, wherein the first hemi-spacer includes a screw insert that receives the screw.

24. The staple according to claim 1, wherein the second hemi-spacer is secured to the second claw with a screw.

25. The staple according to claim 24, wherein the second hemi-spacer includes a screw insert that receives the screw.

26. The staple according to claim 1, wherein the first hemi-spacer interlocks with the second hemi-spacer.

27. The staple according to claim 26, wherein the first hemi-spacer includes an interlocking protrusion.

28. The staple according to claim 26, wherein the first hemi-spacer includes a plurality of interlocking protrusions.

29. The staple according to claim 26, wherein the first hemi-spacer includes an interlocking receptacle.

30. The staple according to claim 26, wherein the first hemi-spacer includes a plurality of interlocking receptacles.

31. The staple according to claim 26, wherein the second hemi-spacer includes an interlocking protrusion.

32. The staple according to claim 26, wherein the second hemi-spacer includes a plurality of interlocking protrusions.

33. The staple according to claim 26, wherein the second hemi-spacer includes an interlocking receptacle.

34. The staple according to claim 26, wherein the second hemi-spacer includes a plurality of interlocking receptacles.

35. The staple according to claim 26, wherein the first hemi-spacer includes an interlocking protrusion and an interlocking receptacle.

36. The staple according to claim 26, wherein the second hemi-spacer includes an interlocking protrusion and an interlocking receptacle.

37. The staple according to claim 1, wherein the first hemi-spacer includes an interlocking protrusion and an interlocking receptacle,
wherein the second hemi-spacer includes an interlocking protrusion and an interlocking receptacle,
wherein the interlocking protrusion of the first hemi-spacer engages the interlocking receptacle of the second hemi-spacer when the first claw and the second claw are in a closed position, and
wherein the interlocking protrusion of the second hemi-spacer engages the interlocking receptacle of the first hemi-spacer when the first claw and the second claw are in a closed position.

38. The staple according to claim 37, wherein the interlocking protrusion of the first hemi-spacer has a tapered surface, and wherein the interlocking receptacle of the second hemi-spacer has a corresponding tapered surface.

39. The staple according to claim 37, wherein the interlocking protrusion of the second hemi-spacer has a tapered surface, and wherein the interlocking receptacle of the first hemi-spacer has a corresponding tapered surface.

40. The staple according to claim 1, wherein the first hemi-spacer is a rectangularly-shaped hemi-spacer.

41. The staple according to claim 1, wherein the second hemi-spacer is a rectangularly-shaped hemi-spacer.

42. The staple according to claim 1, wherein a length of the first hemi-spacer is approximately equal to an inter-spinous process distance.

43. The staple according to claim 1, wherein a length of the second hemi-spacer is approximately equal to an inter-spinous process distance.

44. The staple according to claim 1, wherein a length of the first hemi-spacer is approximately equal to an inter-lumbar transverse process distance.

45. The staple according to claim 1, wherein a length of the second hemi-spacer is approximately equal to an inter-lumbar transverse process distance.

46. The staple according to claim 1, wherein each of the first clamping surface and the second clamping surface has a convex surface.

47. The staple according to claim 1, wherein each of the first clamping surface and the second clamping surface has a concave surface.

48. The staple of claim 1, wherein the first hemi-spacer includes a first surface and the second hemi-spacer includes a second surface, the first surface opposing the second surface when the staple is in a closed position,
wherein the first surface directly abuts the second surface when the staple is in the closed position to prevent movement of the first hemi-spacer in a direction toward the second hemi-spacer and to define a predetermined separation distance between the first clamping surface of the first claw and the second clamping surface of the second claw.

49. The staple of claim 48, wherein the first surface of the first hemi-spacer and the second surface of the second hemi-spacer interdigitate, interlock, and unite when the staple is in the closed position to form an integral wedge defining the predetermined separation distance between the first clamping surface of the first claw and the second clamping surface of the second claw.

50. The staple of claim 49, wherein the first surface of the first hemi-spacer includes at least one protrusion,
wherein the second surface of the second hemi-spacer includes at least one receptacle, and
wherein the protrusion interlocks with the receptacle when the staple is in the closed position.

51. The staple of claim 49, wherein the first surface of the first hemi-spacer includes a first protrusion and a first receptacle,
wherein the second surface of the second hemi-spacer includes a second protrusion and a second receptacle,
wherein the first protrusion of the first surface of the first hemi-spacer interlocks with the second receptacle of the second surface of the second hemi-spacer when the staple is in a closed position, and wherein the second protrusion of the second surface of the second hemi-spacer interlocks with the first receptacle of the first surface of the first hemi-spacer when the staple is in the closed position.

52. The staple of claim 1, wherein the first hemi-spacer and the second hemi-spacer include mirror image interdigitating and interlocking protrusions and receptacles.

53. The staple of claim 1, wherein the ratchet mechanism includes first claw teeth on the top claw and second claw teeth on the bottom claw, the first claw teeth opposing the second claw teeth, the first claw teeth interdigitating with the second claw teeth to limit an opening force of the first claw with respect to the second claw.

54. An interarticulating staple for clamping one of a thoracic/lumbar Spinous Process (SP), a thoracic/lumbar Transverse Process (TP), and cervical Spinous Process (SP), the interarticulating staple comprising:
  a first claw having a first clamping surface;
  a second claw having a second clamping surface;
  a staple pin pivotally connecting the first claw and the second claw;
  ratchet means for limiting an opening force of the first claw with respect to the second claw;
  first spacer means on the first clamping surface of the first claw; and
  second spacer means on the second clamping surface of the second claw and opposed to the first spacer means when the first claw and the second claw are in a closed position,
  wherein the first spacer means interlocks with the second spacer means for providing one of adjacent spinous process separation and distraction.

55. An interarticulating staple for clamping one of a thoracic/lumbar Spinous Process (SP), a thoracic/lumbar Transverse Process (TP), and cervical Spinous Process (SP), the interarticulating staple comprising:
  first claw means pivotally connected to second claw means; and
  ratchet means for limiting an opening force of the first claw means with respect to the second claw means and fixing a position of the first claw means with respect the second claw means; and
  interlocking spacer means on at least one of the first claw means and the second claw means, the interlocking spacer means for providing one of adjacent spinous process separation and distraction.

56. An interarticulating staple for clamping one of a thoracic/lumbar Spinous Process (SP), a thoracic/lumbar Transverse Process (TP), and cervical Spinous Process (SP), the interarticulating staple comprising:
  a first claw having a first clamping surface and a second claw having a second clamping surface, wherein the first clamping surface and the second clamping surface cooperate to clamp a pair of adjacent spinous processes;
  a staple pin pivotally connecting the first claw and the second claw;
  a ratchet mechanism that limits an opening force of the first claw with respect to the second claw;
  a first hemi-spacer on the first clamping surface of the first claw; and
  a second hemi-spacer on the second clamping surface of the second claw and opposed to the first hemi-spacer when the first claw and the second claw are in a closed position,
  wherein the first hemi-spacer and the second hemi-spacer cooperate to interpose and distract the pair of adjacent spinous processes when the first claw and the second claw are clamped on the pair of adjacent spinous processes in the closed position,
  wherein the first hemi-spacer includes a first surface and the second hemi-spacer includes a second surface, the first surface opposing the second surface when the staple is in a closed position, and
  wherein the first surface directly abuts the second surface when the staple is in the closed position to prevent movement of the first hemi-spacer in a direction toward the second hemi-spacer and to define a predetermined separation distance between the first clamping surface of the first claw and the second clamping surface of the second claw.

57. A method of clamping one of a thoracic/lumbar Spinous Process (SP), a thoracic/lumbar Transverse Process (TP), and cervical Spinous Process (SP), the method comprising:
  positioning an interarticulating staple on a pair of adjacent spinous processes, wherein the interarticulating staple comprises:
    a first claw having a first clamping surface and a second claw having a second clamping surface, wherein the first clamping surface and the second clamping surface cooperate to clamp the pair of adjacent spinous processes;
    a staple pin pivotally connecting the first claw and the second claw;
    a ratchet mechanism that limits an opening force of the first claw with respect to the second claw;
    a first hemi-spacer on the first clamping surface of the first claw; and
    a second hemi-spacer on the second clamping surface of the second claw and opposed to the first hemi-spacer when the first claw and the second claw are in a closed position, wherein the first hemi-spacer and the second hemi-spacer cooperate to interpose and distract the pair of adjacent spinous processes when the first claw and the second claw are clamped on the pair of adjacent spinous processes in the closed position; and
  securing the interarticulating staple to the pair of adjacent spinous processes by clamping the first clamping surface and the second clamping surface to the pair of adjacent spinous processes such that the first hemi-spacer and the second hemi-spacer interpose and distract the pair of adjacent spinous processes when the first claw and the second claw are clamped on the pair of adjacent spinous processes in the closed position.

* * * * *